United States Patent [19]
Köcher et al.

[11] Patent Number: 5,290,536
[45] Date of Patent: Mar. 1, 1994

[54] PHENYL SUBSTITUTED 2-THIAZOLYL TETRAZOLIUM SALT INDICATORS

[75] Inventors: Jürgen Köcher, Langenfeld; Klaus Wehling, Wuppertal, both of Fed. Rep. of Germany

[73] Assignee: Miles Inc., Elkhart, Ind.

[21] Appl. No.: 974,174

[22] Filed: Nov. 10, 1992

Related U.S. Application Data

[63] Continuation-in-part of Ser. No. 853,352, Mar. 16, 1992, abandoned, which is a continuation of Ser. No. 585,725, Sep. 19, 1990, abandoned.

[51] Int. Cl.$^5$ .............. C07D 417/04; G01N 33/487; C12Q 1/26
[52] U.S. Cl. .................... 424/7.1; 546/162; 546/276; 548/193; 548/194
[58] Field of Search .............. 548/193, 194; 546/276, 546/162; 424/7.1

[56] References Cited

FOREIGN PATENT DOCUMENTS 239931 10/1987 European Pat. Off. .

OTHER PUBLICATIONS

Johne, Pharazie, 34 (12) 790 (1979).

*Primary Examiner*—Robert Gerstl
*Attorney, Agent, or Firm*—Andrew L. Klawitter; Jerome L. Jeffers

[57] ABSTRACT

Phenyl substituted 2-thiazolyl tetrazolium salt compounds characterized by a reflectance spectrum exhibiting an extended plateau above about 600–650 nm. Such compounds are useful as chromogenic indicators for reducing substances such as NADH. The reflectance plateau confers improved accuracy to analytical assays, particularly for the determination of analytes of medical diagnostic significance, in which a colorimetric response on a reagent carrier matrix is measured by reflectance.

17 Claims, 5 Drawing Sheets

PHENYL SUBSTITUTED 2-THIAZOLYL TETRAZOLIUM SALT INDICATORS

BACKGROUND OF THE INVENTION

This is a continuation-in-part of application Ser. No. 07/853,352 filed Mar. 16, 1992, which in turn is a continuation of application Ser. No. 07/585,725 filed Sep. 19, 1990 both now abandoned.

The present invention relates to chromogenic tetrazolium salt indicator compounds useful in the determination of reducing substances, particularly nicotinamide adenine dinucleotide (NADH).

Tetrazolium salts are well known as chromogenic indicators responsive to reducing substances. Upon reduction, tetrazolium salts are converted into formazan dye products. These indicators have found use in a wide variety of fields, particularly the medical diagnostic field where they have been applied to, among others, cell staining and the determination of analytes in body fluids such as urine, milk, serum, and plasma. Commonly, the determination of body fluid analytes involves an NAD-dependent enzymatic reaction in which NADH is formed as a function of the amount of analyte present in the sample tested. The amount of NADH generated can then be determined by the reductive conversion of an appropriate tetrazolium salt indicator to its formazan dye product.

Within the field of medical diagnostic tests, tetrazolium salt indicators are useful in a variety of different product types. One particular type is the reagent strip. This product is a solid state device comprising a paper or other porous carrier matrix which is impregnated or otherwise incorporated with chemical reagents responsive to a particular analyte, for example, glucose or cholesterol. The incorporated reagent system includes a chromogenic indicator which develops color, or changes color, as a function of the amount of analyte in a sample applied to the matrix. The resulting colorimetric response can be observed visually to give qualitative or semi-quantitative readings. Quantitative results can be obtained by reading the reflectance of the matrix surface at one or more defined wavelengths with an appropriate instrument (reflectance meter).

There is a recognized need to develop tetrazolium indicators having strong absorbance at wavelengths longer than the absorbances of major interferants that can be present in the test sample. For instance, interference from hemoglobin coloration is a particular concern where the sample is whole blood. Indicators having significant absorption above about 640 nm are required in order to substantially overcome hemoglobin interference. The commonly used tetrazolium salt indicators are 2-(4-iodophenyl)-3-(4-nitrophenyl)-5-phenyltetrazolium chloride (INT), 3-(4,5-dimethylthiazol-2-yl)-2,5-diphenyltetrazolium chloride (MTT), and 2,2',5,5'-tetraphenyl-3,3'(3,3'-dimethoxy-4,4'-diphenylene) ditetrazolium chloride (NBT). These compounds show maximum absorption (UVmax) in the range of 465-605 nm. Those indicators having maximum absorption at longer wavelength so that the midpoint of their maximum absorption range is at least about 640 nm are preferred for use in the analysis of blood samples.

Another shortcoming of the conventionally used prior art tetrazolium salt indicators relates to the evolution of the instrumentation used to measure their colorimetric response. Rapid advancements are being made in developing smaller, less expensive reflectance meters. One of the more costly components of such meters is the optical system which comprises a light source, a filter or other spectral element for selecting or limiting the wavelength of incident or reflected light, and a sensor. Significant cost savings could be realized by eliminating or combining functions of the optical system elements or by using less expensive components, e.g., LEDs as illuminating light sources. However, commercially available LEDs emit light having a center wavelength that can vary significantly due to manufacturing variances and temperature dependence. The conventionally used tetrazolium salt indicators INT, MTT, and NBT have reflectance spectra which are strongly sloped in the region above their UVmax. Accordingly, without individually calibrating both each instrument, to account for manufacturing variability in the LED, and each test run, to account for variance due to temperature, large errors can be introduced into the assay result.

The following are representative of the prior art teachings concerning the use of various tetrazolium salts in colorimetric analysis. Tanaka et al, Japanese Kokai Tokkyo Koho JP 61000084 (Chem. Abst. 104:203469y) describes the detection of glucose using a formazan chelate obtained by the reduction of 2-(2-benzothiazolyl)-3-(carboxyphenyl)-5-phenyl-2H-tetrazolium halide in the presence of nickel (II). Limbach et al, German DE 3,247,894 (Chem. Abst. 101:125929v) relates to the use of INT in glucose assays. Rittersdorf et al, German DE 2,147,466 describes the use of seven 2-(2-benzothiazolyl)-3-phenyl-5-(4-[trimethylammonio]phenyl) tetrazolium salts in the determination of reducing substances such as reducing sugars, ascorbic acid, and ketosteroids.

The variety of 2-thiazolyl tetrazolium salts and/or their corresponding formazans known in the literature are represented by the following. Serebryakova et al, Khim. Geterotsikl. Soedin. 10:1403–1405 (1970) describe the synthesis and chromatic properties of benzothiazolyl-3-phenyl-(methyl)-5-p-nitro(dimethylamino)-phenylformazans. The authors state that both an electron withdrawing nitro group at the para-position of the 5-phenyl and a benzothiazolyl group at the 1-position provides a bathochromic shift. Lipunova et al, Khim. Geterotsikl. Soedin. (1971) 831–835 compare the bathochromic effect of a 5-naphthyl or o-tolyl group on the visible spectrum of 1-benzothiazolylformazans. Johne et al, Pharmazie 34:790–794 (1979) describe certain 2-(4,5-diphenyl)thiazol-2-yl tetrazolium salts.

SUMMARY OF THE INVENTION

The present invention provides thiazolyl tetrazolium salts which upon reduction yield formazans having new and improved optical properties. The compounds of the present invention are of the general Formula A:

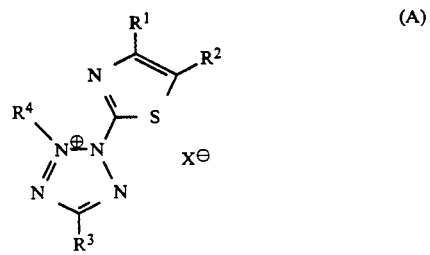

wherein one or both of $R^1$ and $R^2$ are unsubstituted phenyl or phenyl substituted with, independently, alkoxy, aryloxy, alkyl, amido, alkylamido, arylamido, alkylthio, arylthio, amino, carbamoyl, carbalkoxy, carboxy, cyano, halo, nitro, sulfo, sulfonamido, sulfamoyl, trialkylammonio, or ureido, and if only one is substituted or unsubstituted phenyl, the other is hydrogen or alkyl, and if $R^2$ is substituted or unsubstituted phenyl, then $R^1$ can also be styryl or naphthyl; wherein $R^3$ is selected from:

($a_1$) residues of Formula B:

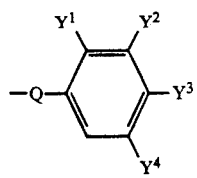
(B)

wherein Q is a bond of —CH=CH—, and wherein
(i) $Y^1$ is alkoxy, aryloxy, alkyl, amido, alkylamido, arylamido, alkylthio, arylthio, halo, or hydrogen, $Y^2$ is alkoxy, aryloxy, alkyl, amido, alkylamido, arylamido, alkylthio, arylthio, amino, carbamoyl, carbalkoxy, carboxyl, cyano, halo, hydrogen, nitro, sulfo, sulfonamido, sulfamoyl, trialkylammonio, or ureido, $Y^3$ is alkoxy, aryloxy, alkyl, amido, alkylamido, arylamido, alkylthio, arylthio, amino, carbamoyl, carbalkoxy, carbaryloxy, carboxyl, cyano, halo, hydrogen, hydroxyl, nitro, sulfo, sulfonamido, sulfamoyl, trialkylammonio, or ureido, and $Y^4$ is alkoxy, aryloxy, halo, or hydrogen, or
(ii) $Y^2$ and $Y^3$ together form methylenedioxy or imidazo and $Y^1$ and $Y^4$ are hydrogen,
($b_1$) 2, 3, or 4-pyridyl,
($c_1$) 2 or 3-thienyl, and
($d_1$) 2 or 3-furanyl;
wherein $R^4$ is selected from:
($a_2$) residues of Formula C:

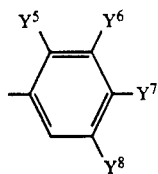
(C)

wherein $Y^5$ is alkoxy, aryloxy, alkyl, amido, alkylamido, arylamido, alkylthio, arylthio, halo, hydrogen, nitro, or ureido, $Y^6$ is alkoxy, aryloxy, alkyl, amido, alkylamido, arylamido, alkylthio, arylthio, carbamoyl, carbalkoxy, carboxyl, cyano, halo, hydrogen, nitro, sulfo, sulfonamido, sulfamoyl, trialkylammonio, or ureido, $Y^7$ is alkoxy, aryloxy, amido, alkylamido, arylamido, alkylthio, arylthio, carbamoyl, carbalkoxy, carbaryloxy, carboxyl, cyano, hydroxyl, nitro, phenylazo, sulfo, sulfonamido, sulfamoyl, or ureido, and $Y^8$ is alkoxy, alkyl, halo, hydrogen or nitro,
($b_2$) residues of Formula D:

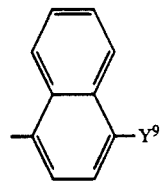
(D)

wherein $Y^9$ is alkoxy, aryloxy, alkyl, amido, alkylamido, arylamido, alkylthio, arylthio, carbamoyl, carbalkoxy, carboxyl, cyano, halo, hydrogen, nitro, phenylsulfo, sulfonamido, sulfo, sulfonamido, sulfamoyl, trialkylammonio, or ureido,
($c_2$) 2, 4, 6, or 8-quinolyl, or 2-methylquinolyl, and
($d_2$) anthranyl; and
wherein X is a counteranion;
but provided that in the case where $R^1$ and $R^2$ are both unsubstituted phenyl, (A) when Q is —CH=CH— and $Y^1$, $Y^2$, $Y^3$ and $Y^4$ are all hydrogen, then $R^4$ is not 2-carboxyphenyl, (B) when $Y^5$ and $Y^8$ are both hydrogen and one of $Y^6$ or $Y^7$ is carboxyl or sulfo and the other is hydrogen, then $R^3$ is not unsubstituted phenyl, 2-pyridyl, or 3-pyridyl, and (C) when $R^4$ is unsubstituted naphthyl, then $R^3$ is not unsubstituted phenyl.

The present compounds are characterized by a reflectance spectrum exhibiting an extended plateau above about 600 nm, preferably above about 650 nm. Such a reflectance plateau confers improved accuracy to reflectance-read reagent strip analytical assays, particularly where the optical measurement system has a variable central wavelength.

DESCRIPTION OF THE PREFERRED EMBODIMENTS

Figure 1:
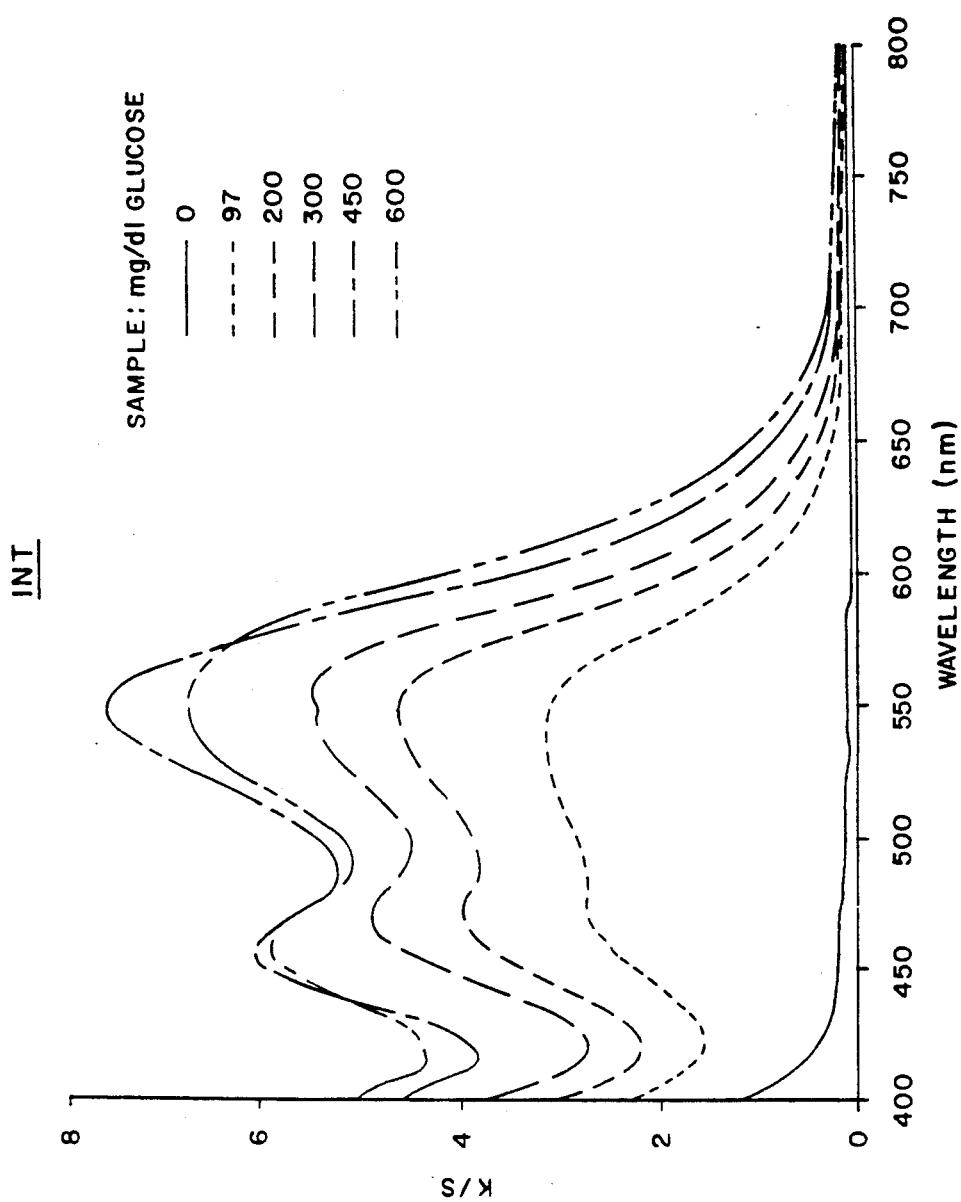
FIGS. 1-4 show the reflectance spectra of the formazans produced upon reduction of the prior art tetrazolium salts INT, MTT, and NBT at various concentrations of glucose.
Figure 2:
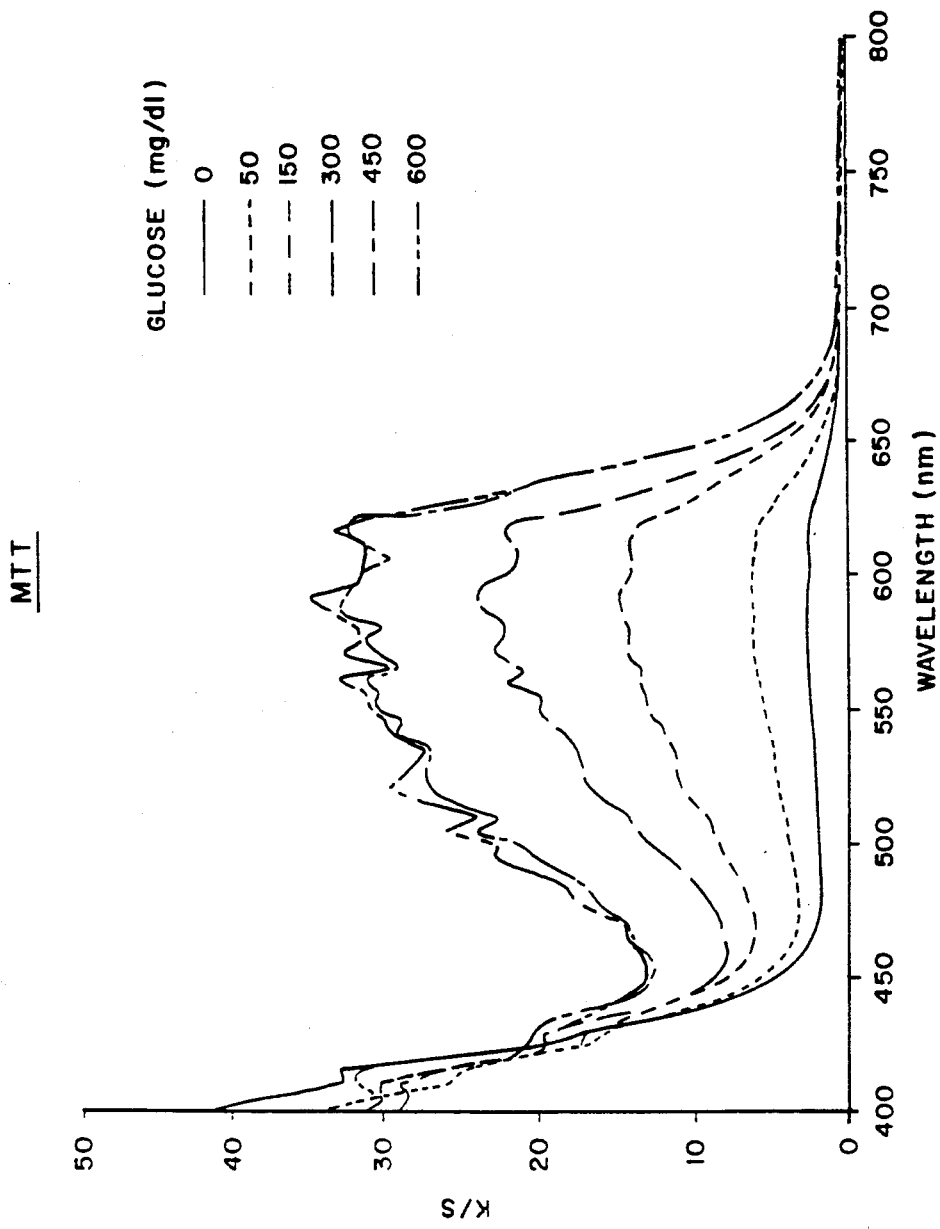
Figure 3:
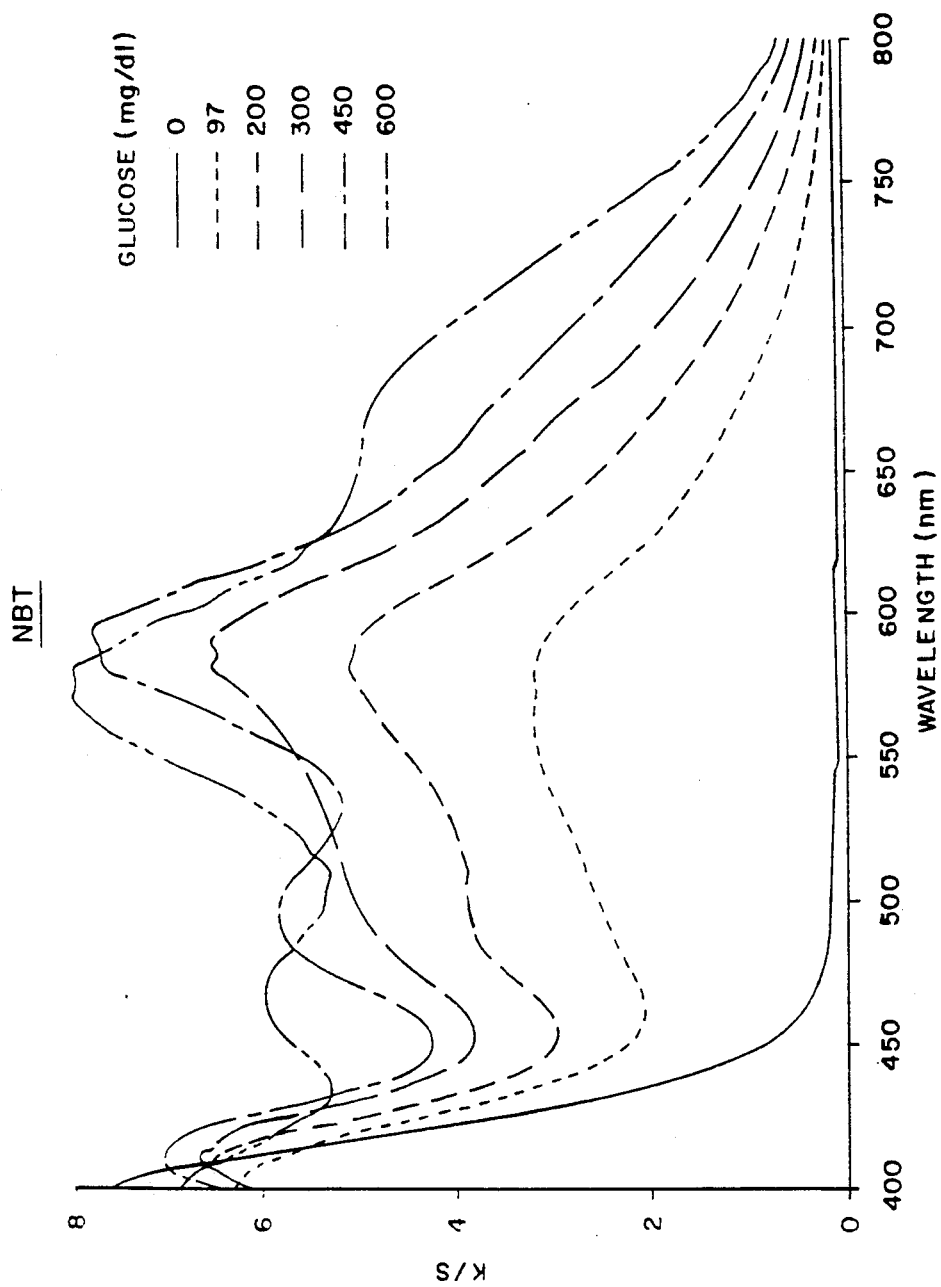
Figure 4:
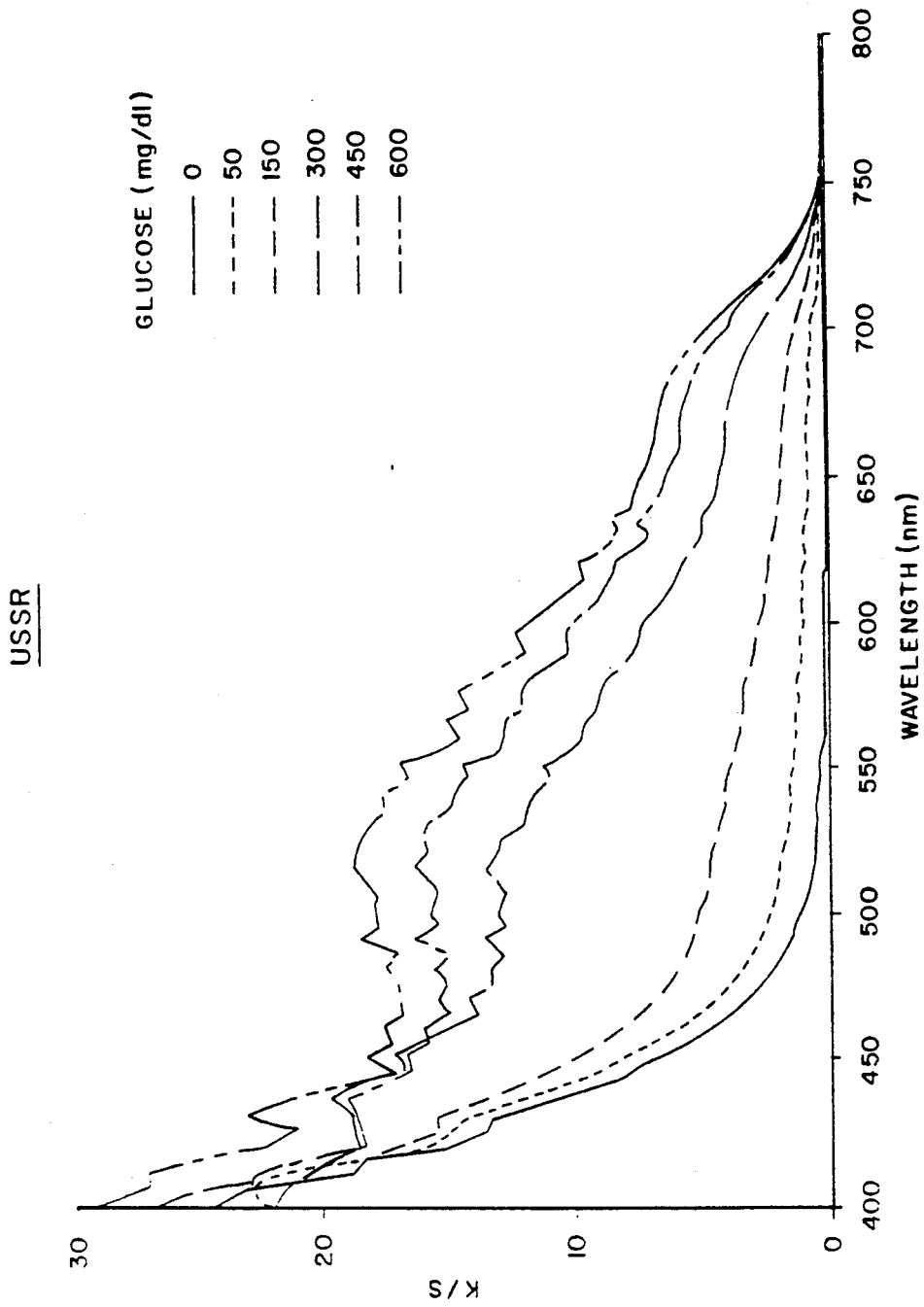

The following definitions shall apply to the subject disclosure:

"$C_{1-4}$"—used to limit a residue, e.g., $C_{1-4}$ alkyl, to those forms which contain between 1 and 4 relevant atoms, e.g., carbon atoms, inclusive.

"Alkyl"—linear and branched hydrocarbon residues of the general formula $C_nH_{2n+1}$, preferably "lower alkyl" such as the $C_{1-4}$ alkyls of methyl, ethyl, n-propyl, iso-propyl, n-butyl, iso-butyl, and tert-butyl, as well as higher alkyls such as n-pentyl, n-hexyl, and the like.

"Alkoxy"—the residue —OR wherein R is alkyl.

"Alkylamido"—the residue —NRC(=O)$R^1$ wherein R and R', same or different, are alkyl.

"Alkylthio"—the residue —SR wherein R is alkyl.

"Amido"—the residue —NHC(=O)H.

"Amino"—the residue —NRR$^1$ wherein R and R', same or different, are hydrogen or alkyl. "Aryl"—organic residues derived from an aromatic carbocyclic or heterocyclic ring or ring system by removal of a hydrogen atom attached to such ring or ring system, e.g., phenyl, naphthyl, pyridyl, oxazolyl, quinolyl, thiazolyl, thienyl, furanyl, and the like.

"Arylamido"—the residue —NRC(=O)R' wherein R and R', same or different, are aryl.

"Aryloxy"—the residue —OR wherein R is aryl.

"Arylthio"—the residue —SR wherein R is aryl.

"Carbalkoxy"—the residue —C(=O)OR wherein R is alkyl. "Carbaryloxy"—the residue —C(=O)OR wherein R is aryl.

"Carbamoyl"—the residue —C(=O)NRR' wherein R and R', same or different, are hydrogen or alkyl.

"Carboxyl"—the residue —C(=O)OH.

"Halo"—fluoro, chloro, and bromo.

"Imidazo"—the divalent residue —N=CH—NH—.

"Methylenedioxy"—the divalent residue of the formula —O—CH$_2$—O—.

"Phenylazo"—the residue —N=N—phenyl.

"Styryl"—the residue —CH=CH—R wherein R is aryl.

"Sulfo"—the residue —SO$_3$.

"Sulfamido"—the residue —NRSO$_2$R' wherein R and R', same or different, are alkyl, aryl, or hydrogen.

"Sulfamoyl"—the residue —SO$_2$NRR' wherein R and R', same or different, are alkyl, aryl, or hydrogen.

"Trialkylammonio"—the residue —NR$^3$+ wherein R is alkyl.

"Ureido"—the residue —NRC(=O)NR' wherein R and R', same or different, are alkyl, aryl, or hydrogen.

It will be understood that, unless otherwise specifically stated, it is intended that the use of the above terms in the case of residues that can be substituted or unsubstituted, e.g., alkyl, aryl, phenylazo, and styryl, shall include the reasonably substituted forms of such residues as well as their unsubstituted forms. Reasonable substitutions which will produce useful compounds of the present invention will be evident to one of ordinary skill in the art, and will include such substituents, without limitation, as alkoxy, amino, alkylthio, carbalkoxy, carboxy, hydroxy, sulfo, and sulfamoyl, to name just a few.

PREFERRED R$^1$ AND R$^2$ RESIDUES

While the R$^1$ and R$^2$ phenyl groups can be multiply substituted, in practice, only one or two substituents will normally be present. In the case of a single substitution, it will preferably be in the para-position. Further, from the standpoints of synthesis and reflectance spectrum properties of the formazan, preferable compounds are those wherein (i) both of R$^1$ and R$^2$ are unsubstituted phenyl or phenyl para-substituted with the same group selected from alkoxy, aryloxy, alkyl, amido, alkylamido, arylamido, alkylthio, arylthio, carbamoyl, carbalkoxy, carbaryloxy, carboxy, cyano, halo, trialkylammonio, and ureido, or (ii) one of R$^1$ and R$^2$ is unsubstituted phenyl or phenyl para-substituted with alkoxy or aryloxy and the other is hydrogen.

Based on the properties of compounds that have been prepared, the most preferred compounds are those wherein both of R$^1$ and R$^2$ are unsubstituted phenyl or one is unsubstituted phenyl and the other is phenyl para-substituted with C$_{1-4}$ alkoxy; or wherein R$^1$ is unsubstituted phenyl or phenyl para-substituted with C$_{1-4}$ alkoxy, C$_{1-4}$ alkyl, or halo, and R$^2$ is hydrogen.

PREFERRED R$^3$ AND R$^4$ RESIDUES

From the standpoints of synthesis and reflectance spectrum properties of the formazan, R$^3$ will preferably be selected from:

(A$_1$) residues of Formula E:

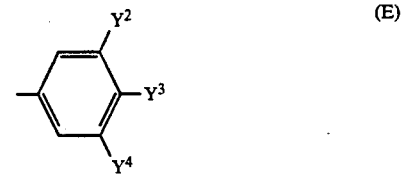

wherein (i) Y$^2$, Y$^3$, and Y$^4$ are each C$_{1-4}$ alkoxy, (ii) Y$^4$ is hydrogen and Y$^2$ and Y$^3$ are both C$_{1-4}$ alkoxy or together form methylenedioxy, or (iii) Y$^2$ and Y$^4$ are both hydrogen and Y$^3$ is C$_{1-4}$ alkoxy, C$_{1-4}$ alkyl, C$_{1-4}$ alkylamido, alkylthio, C$_{1-4}$ alkylthio, carbamoyl, carb(C$_{1-4}$)alkoxy, carboxyl, cyano, halo, hydrogen, nitro, tri(C$_{1-4}$)alkylammonio, or ureido, and (b$_1$) 2 or 3-thienyl.

Based on the properties and synthesis of compounds that have been prepared, it is most preferred that R$^3$ be selected from:

3,4,5-trimethoxyphenyl,
3,4-dimethoxyphenyl,
3,4-methylenedioxyphenyl,
4-methoxyphenyl,
4-acetamidophenyl,
4-methylthiophenyl,
4-phenyl,
4-halophenyl,
4-cyanophenyl,
4-nitrophenyl,
2-thienyl, and
3-thienyl.

The preferred R$^4$ residues are: (a$_2$) residues of Formula C, supra, wherein (i) Y$^5$ is hydrogen and each of Y$^6$, Y$^7$, and Y$^8$ is C$_{1-4}$ alkoxy.

(ii) Y$^5$ and Y$^8$ are both hydrogen and Y$^6$ and Y$^7$ are both C$_{1-4}$ alkoxy or together form methylenedioxy, (iii) Y$^5$, Y$^6$ and Y$^8$ are each hydrogen and Y$^7$ is C$_{1-4}$ alkoxy, C$_{1-4}$ alkylamido, C$_{1-4}$ alkylthio, benzamido, carbamoyl, carb(C$_{1-4}$)alkoxy, carboxyl, cyano, hydroxyl, nitro, phenylazo, sulfo, sulfonamido, sulfamoyl, or ureido;

(iv) Y$^5$ is alkoxy or alkyl, Y$^6$ and Y$^8$ are both hydrogen, and Y$^7$ is C$_{1-4}$ alkoxy, C$_{1-4}$ alkylamido, C$_{1-4}$ alkylthio, benzamido, carbamoyl, carb(C$_{1-4}$)alkoxy, carboxyl, cyano, hydrogen, nitro, phenylazo, or ureido;

(v) Y$^5$ and Y$^6$ are C$_{1-4}$ alkoxy; or (vi) Y$^5$ and Y$^8$ are C$_{1-4}$ alkoxy and Y$^7$ is C$_{1-4}$ alkylamido or benzamido;

(b$_2$) residues of Formula D, supra, wherein Y$^9$ is C$_{1-4}$ alkoxy, C$_{1-4}$ alkyl, C$_{1-4}$ alkylamido, C$_{1-4}$ alkylthio, cyano, halo, hydrogen, nitro, sulfo, sulfonamido, or ureido, and (c$_2$) 8-quinolyl. Based on the properties and synthesis of compounds that have been prepared, it is most preferred that R$^4$ be selected from:

3,4,5-trimethoxyphenyl,
3,4-dimethoxyphenyl, 2,4-dimethoxyphenyl,
3,4-methylenedioxyphenyl,
4-methoxyphenyl,
4-acetamidophenyl,
4-methylthiophenyl,
4-carboxyphenyl,
4-nitrophenyl,
2-methoxyphenyl,
2-methoxy-4-carboxyphenyl,
2,5-dimethoxyphenyl,
2,5-dimethoxyphenyl-4-benzamidophenyl,
1-naphthyl,
4-nitro-1-naphthyl,
4-methoxy-1-naphthyl,
8-quinolyl,
2-methyl-4-carboxyphenyl,
4-carbmethoxyphenyl,
4-cyanophenyl, and

COUNTERANION

The selection of the counteranion will be based primarily on considerations of stability and solubility of the particular tetrazolium salt of interest. In general, one can select from such counteranions as the inorganic anions chloride, bromide, iodide, nitrate, fluoroborate, perchlorate, and sulfate, as well as organic anions such as acetate, oxalate, tartrate, and aryl sulfonates'(benzene sulfonate, tosylate).

SYNTHETIC METHODS

Tetrazolium salts are prepared by methods well known in the literature (Hooper, W. D., Rev. Pure and Appl. Chem., 1969, 19, 221; Putter, R., in Methoden der Organischen Chemie, Houben-Weyl-Muller ed., Thieme Verlag: Stuttgart, 1965, Bd. 10/3, p. 633; Nineham, A. W. Chem. Rev., 1955, pp. 355–483). In general, the tetrazolium salts of the present invention are prepared by first reacting a 2-hydrazinothiazole with an aldehyde and then treating the resulting hydrazone with a diazotized aniline. The resulting formazan is then oxidized to the tetrazolium salt by well known methods. Consequently, the synthesis involves three principal starting materials, the aldehyde, the aniline, and the 2-hydrazinothiazole.

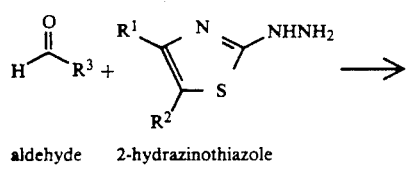

aldehyde    2-hydrazinothiazole

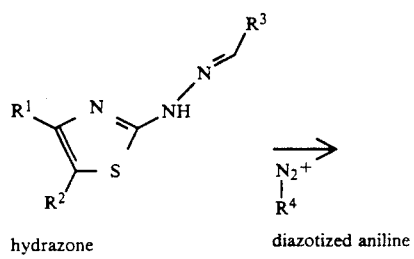

hydrazone    diazotized aniline

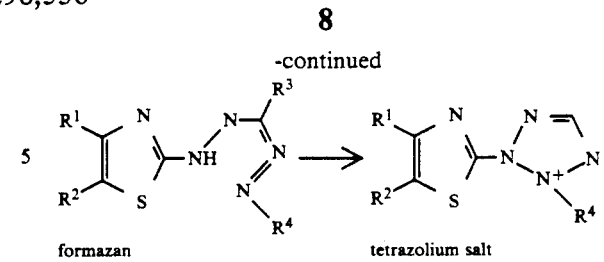

formazan    tetrazolium salt

Preparation of 2-hydrazinothiazoles 4,5-Diphenyl-2-hydrazinothiazoles are prepared by two methods. One is by first forming a benzoin condensation (1) product between two aldehydes (Ide, W. S., Buck, J. S., Org. React., 1948, Vol. 4, 269). Benzoins not available by this method are prepared from the condensation of a phenyl substituted "acyl anion equivalent" with another aldehyde followed by removal of the carbonyl protecting group (Bertz, S., J. Chem. Soc., Chem. Comm., 1980, 17, 831). A specific example is the condensation of the metallated O—trimethylsilylcyanohydrin (3) with an aryl aldehyde. The product (4) is deprotected using aqueous acetic acid to afford the benzoin product (1).

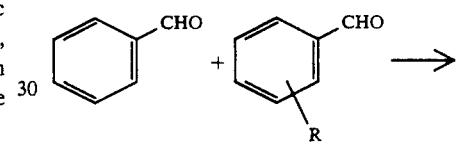

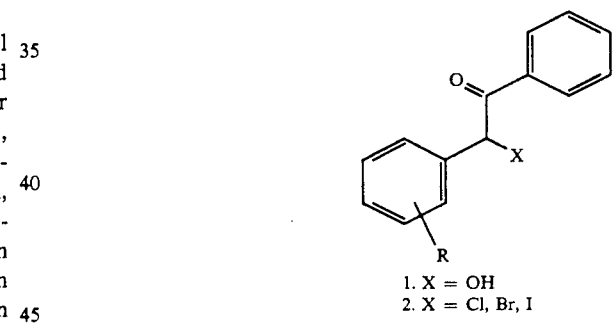

1. X = OH
2. X = Cl, Br, I

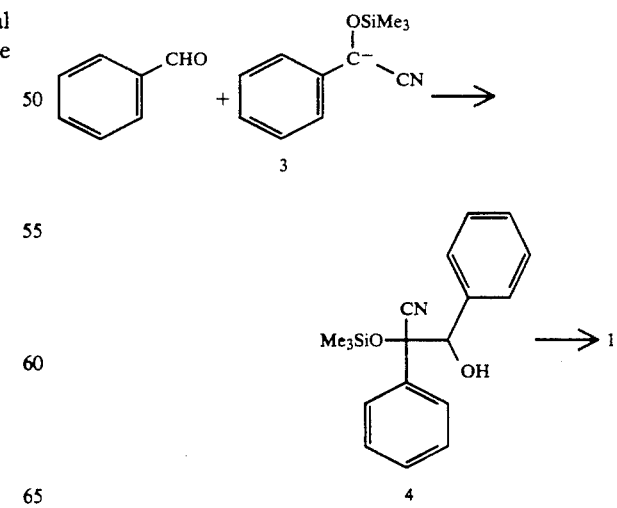

The benzoin products are then converted into the halide (2) using conventional reagents such as thionyl chloride to produce the α-haloketones (2) which react with thiourea to produce 4,5-diphenyl-2-aminothiazoles (Traumann, V., Liebigs Ann. Chem., 1888, 250, 31, Dodson et al., J. Am. Chem. Soc., 1945, 67, 2442). These can be converted to the 2-hydrazino compounds with hydrazine as described for the benzo examples.

The same α-haloketones react with thiocyanate to produce α-thiocyanoketones (5) which readily cyclize. For instance, when treated with hydrogen chloride gas, the 2-chlorothiazoles (6) are obtained which react with hydrazine to give the 2-hydraziinothiazoles.

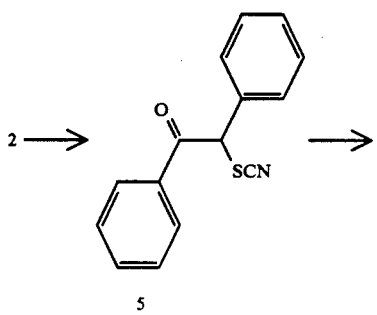

Alternatively, the α-haloketones may be used to directly yield the necessary hydrazone (8) by treating the haloketone with an N-arylthiosemicarbazone (7) (Johne, S., Schaks, A., Hartung, S., Scharf, K.-D., and Nover, L., Pharmazie, 1979, 34, 790).

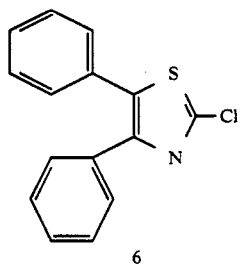

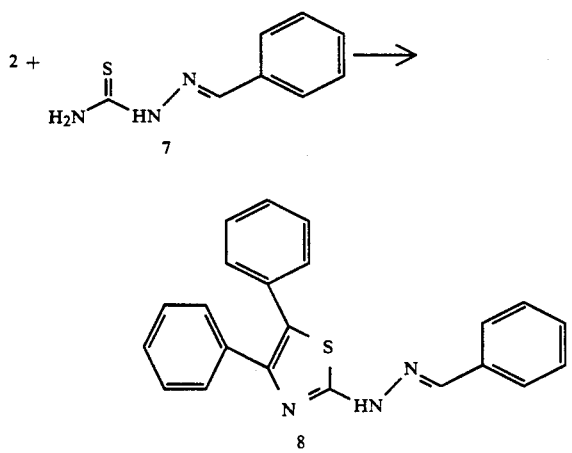

Thiazoles substituted in the 4-position with aryl and the 5-position with alkyl or hydrogen may be prepared similarly with a α-haloketone and thiosemicarbazone or thiourea.

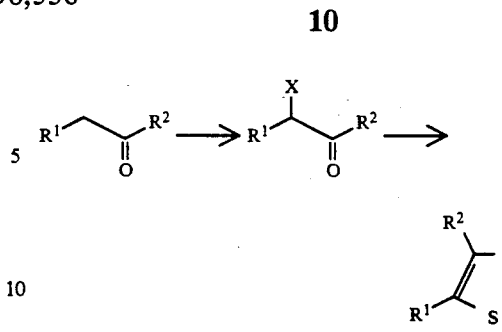

$R^1$ = alkyl, hydrogen
$R^2$ = aryl

Preparation of Aldehydes

The aldehydes are obtained from commercial sources or can be prepared by methods familiar to one of ordinary skill in the art.

For instance, aldehydes may be prepared by benzylic oxidation of an arylmethane (March, J., Advanced Organic Chemistry Third Edition; John Wiley and Sons: New York, 1985; p. 1079), reduction of an aryl acid chloride (Ibid. p. 396) or aryl acid derivative, (Larock, R. C., Comprehensive Organic Transformations; VCH: New York, 1989; pp. 604–605).

Aryl halides may also be used to synthesize aldehydes. In this method, a transmetallation reaction produces an arylmetallic species which can be treated with a variety of reagents, such as dimethylformamide, to produce the aldehyde (Ibid, p. 681–683).

The aforementioned aryl aldehydes, acids, methanes, and halides, may be derivatized with a variety of functional groups prior to their transformation into tetrazolium salts. This may be accomplished by aromatic nucleophilic substitution (March, J., Advanced Organic Chemistry Third Edition; John Wiley and Sons: New York, 1985; pp. 576–607), aromatic electrophilic substitution (Ibid., pp. 447–511) or heteroatom-directed metallation reactions (Gschwend, H. W., Rodriguez, H. R., in Organic Reactions, John Wiley and Sons: New York, 1979; Vol. 26, 1).

In cases where the aldehyde piece of the tetrazolium salt contains a phenol or amine, the groups must be protected so that there is not a reaction between these and the diazotized aniline or oxidizing reagent used to prepare the tetrazolium salt.

This can be accomplished by protecting a hydroxyaryl aldehyde as an acetate, performing the reaction sequence to make the formazan, and then hydrolyzing the acetate at pH 10. Acidification to pH 5 and then filtration produces the desired formazan.

Where the resulting phenol formazan reacts with oxidizing agent in the tetrazolium salt preparation, the phenol may be protected by an acid labile group such as dihydropyran (Greene, T. W., Protective Groups in Organic Synthesis, John Wiley and Sons: New York; 1981, pp. 87–113) and then removed by stirring the tetrazolium salt in acidic conditions.

Similarly amines on the aldehyde piece must be protected to prevent their reaction. This is best accomplished by using an acid labile carbamate (Ibid, pp. 218–247) which is later removed by stirring the tetrazolium salt under acidic conditions.

Preparation of Aryl Amines

Aryl amines may be prepared by reduction of the corresponding nitro or azide compound (Larock, P. C., Comprehensive Organic Transformations; VCH: New York, 1989; pp. 412–415 or 409–410), reaction between an arylmetallic compound and an electrophilic nitrogen reagent, (Ibid., pp. 399–400), or rearrangement of acyl azides or oxidized amides (Ibid., pp. 431–432).

As in the aldehyde case, electrophilic and nucleophilic aromatic substitution can be used to introduce different functional groups into the aryl amine or synthetic precursor.

USE OF THE COMPOUNDS

The principal use of the tetrazolium salt compounds of the present invention are as chromogenic indicators for detecting reducing substances. In particular, the present compounds are advantageous in the detection of NADH. As such, since NADH is produced in enzyme-catalyzed detection reactions specific for various biochemical substances, the present compounds are particularly useful in medical diagnostic tests. However, in general other reducing substances can also be detected, such as hydrogen sulfide gas, diborane, arsenic hydride, or phosphorus hydride.

The present compounds have been particularly found to exhibit an extended plateau in their reflectance spectrum above about 600 nm. The most preferred indicator compounds of the present invention have a plateau above about 640 nm (i.e., the midpoint of the flattest 50 nm wide portion lies above about 640 nm). Such a reflectance plateau confers improved accuracy to analytical tests based on the measurement of reflectance from a reagent strip.

Reagent strips are known in the art as analytical devices comprising a solid carrier matrix incorporated with a test composition that produces a color change in response to contact with a liquid test sample containing the analyte of interest. Such test composition, in the case of the present invention, comprises (a) a reagent or reagents which react with the analyte to produce a reducing substance, and (b) a 2-thiazolyl tetrazolium salt as described herein which is reducible by such reducing substance to produce a chromogenic formazan dye product. The color response of such reagent strips can be observed visually to give semi-quantitative values, however, quantitative results are obtained by measuring the reflectance of the carrier matrix at a predetermined wavelength. Such measurements involve irradiating the reacted carrier matrix with a light source and sensing the reflectance of the carrier matrix by measuring reflected light with a detector element.

The finding of tetrazolium salt indicators having a reflectance plateau is used to particular advantage where reflectance from a reagent strip is read using an instrument which is subject to variability in the central wavelength of its optical system (the combination of light source, detector element, spectral control elements, e.g., filters, and other components). Variability in the central wavelength of the optical system can be caused by a variety of factors, for example, variability in the central wavelength of the principal spectral control element such as the illuminating light source or filters. For instance, where light emitting diodes (LEDs) are used as the light source, the wavelength of emitted light will typically vary $\pm 4$ nm within an instrument, and up to $\pm 8$ nm between LEDs in different instruments, due to manufacturing variability. Moreover, LEDs are susceptible to variable central wavelength due to temperature effects as well. Where broad band light sources are used with filters to provide spectral control of the central wavelength, variability within an instrument is typically under 1 nm, however, between instrument variability can be as high as $\pm 6$ nm. Thus, the present invention is applicable in those situations where the central wavelength of the light reaching the detector element in the instrument is susceptible to variations in the range of about $\pm 5$ nm.

In the making of a reagent strip for use in the present invention, selection of the carrier matrix, the test reagents which react with analyte to produce the reducing substance, and the method by which such reagents and the tetrazolium indicator are incorporated with the carrier matrix are matters well known in the art of reagent strips. For the sake of reciting just a few examples, typical carrier matrices are porous and absorbent paper, cloth, glass fiber filters, polymeric membranes and films, and the like. Incorporation methods include impregnation of a formed carrier matrix with a solution, suspension, or other liquid form of the test composition, in one or more steps, followed by drying of the matrix; formation of a matrix in the presence of one or more of the components of the test composition, e.g., by casting or layering solutions of film or membrane forming formulations.

The present invention will now be illustrated, but is not intended to be limited by, the following examples.

EXAMPLES

A. Compound Synthesis

Hydrazone Preparations

Preparation of aryl aldehyde 4,5-diarylthiazol-2-yl hydrazones and aryl aldehyde 4-aryl-5-alkyl or hydrogen thiazol-2-yl hydrazones.

A mixture of 50 mmol of the thiosemicarbazone, 50 mmol of the α-chloroketone and 100 mmol of pyridine in 200 mL of ethanol was refluxed for one hour. The mixture was cooled to room temperature and then filtered to yield the hydrazone.

Preparation of aryl aldehyde 4-styryl-5-arylthiazol-2-yl hydrazones.

Compounds of the type 1,4-diaryl-2-oxo-3-butene were prepared by the method of S. A. Fine and P. D. Pulaski in J. Org. Chem. 38, 1747 (1973). Following the procedure of P. L. Southwick and D. I. Sapper in J. Org. Chem. 1926 (1954), a mixture of 130 mmol of a 1,4-diaryl-2-oxo-3-butene, 130 mmol of iodine and 260 mmol of a thiosemicarbazone was refluxed in 1.2 L of ethanol for 5 hours. The mixture was cooled to room temperature and filtered to yield the hydrazone.

Formazan Preparation

The diazonium salt is first prepared by cooling a slurry or solution of 8.5 mmol of the amine in 60 mL of 3N HCl to 5° C. Sodium nitrite (0.70 g, 10.15 mmol) in 5 mL of water is then added dropwise. After stirring for 30 minutes, the mixture added dropwise to a cold ($-25°$ C.) mixture of 8.5 mmol of the hydrazone in 120 mL of 1:1 (v/v) DMF-pyridine. The reaction is not allowed to warm beyond $-15°$ C. during the addition. The mixture is allowed to warm to room temperature while stirring for two hours. Filtration produces the formazan as a black solid. Impurities can be removed by repeated washing with methanol or refluxing the solid in methanol and filtering while hot.

Tetrazolium Salt Preparation

A slurry of 1.5 mmol of the formazan is stirred with 20 mL of acetic acid and 4 mL of isoamyl nitrite for a period of 16–48 hours. The mixture is then filtered to yield the tetrazolium salt. In cases where the salt does not precipitate, dilution with ether caused precipitation.

B. Preparation of Reagent Strips

Indicators were impregnated into a reagent strip and tested with a solution containing a known quantity of glucose or NADH. The reagent strip consists of a polystyrene handle onto which a single reagent pad is attached. The reagent pad was 0.2×0.2" square and contains reagents allowing for a color change which was instrumentally read when an aliquot of sample containing glucose was applied. The dry-phase reagent pad is a solid support composed of cellulosic fibers or a nylon membrane as examples. The reagent pad was impregnated first with a solution of the tetrazolium salt of interest (0.8M/L) and detergent (0.3%) in a solvent such as methanol. The second solution impregnated into the reagent pad contains the following components:

| | |
|---|---|
| Glucose Dehydrogenase (GDH) | 0.8 U/L |
| Diaphorase (DPH) | 0.8 U/L |
| NAD | 0.03 Mol/L |
| PIPES Buffer | 0.15 Mol/L |
| Detergent | 0.5% |

About 0.01 ml of several test solutions (serum, plasma, aqueous) containing at least five different glucose or NADH concentrations between 0 and 33 mM/L was applied to the center of the dried reagent pad. After a lag time of about 60 seconds, the reflectance spectra of each indicator was measured at 5 nm increments over the wavelength range of 400 to 1100 nanometers.

C. Utility Data

Following is a table of spectral and other analytical data pertaining to various synthesized tetrazolium salts of the present invention. The compounds are organized, in order, by the form of their thiazolyl residue, then by their $R^4$ substituent and finally by their $R^3$ substituent. For example, the first compound presented is A.1.a) and is of the Formula A wherein $R^1$ and $R^2$ are both 4-methoxyphenyl, $R^4$ is 4-carboxyphenyl, and $R^3$ is 2-thienyl; the second compound, B.1.a), has a different thiazolyl residue ($R^1$ and $R^2$ are both unsubstituted diphenyl), $R^4$ is carboxyphenyl, and $R^3$ is 3,4-methylenedioxyphenyl; and so forth.

The reflectance spectrum of tetrazolium salts is understood to be dependent upon the environment in which they are observed or measured. For purposes of comparison between individual tetrazolium salts, the data below include a measurement of the relative flatness of the flattest portion of the reflectance spectrum at wavelengths greater than 600 nm, which spectrum is generated using a glucose or cholesterol reagent strip prepared as described in Part B above. The relative flatness of the spectrum is expressed in the data in K/S units normalized for the level of analyte detected as defined below.

K/S is defined by the equation $$K/S = \frac{(1-R)^2}{2R}$$

wherein R is instrumentally read reflectance units. Percent change in K/S is the change, expressed as a percentage, over a 50 nm range divided by the average of the high and low K/S values over the range.

The plateau property of the present compounds shall be understood, for the purposes of this invention, as a percent change in reflectance spectrum (expressed in terms of K/S as defined in the paragraph above) of less than about 17% over a 50 nm wavelength span whose midpoint is at a wavelength above about 640 nm. The more preferable compounds exhibit a plateau having a percent change in K/S of less than about 10% over the 50 nm wavelength span. Most preferred are those tetrazolium salt indicators exhibiting a percent change in K/S of about 5% or less over the 50 nm wavelength span. Compounds having a more sloped reflectance spectrum are nonetheless preferred where the flattest portion begins at a wavelength above 650 nm, preferably above 675 nm.

Figure 5:
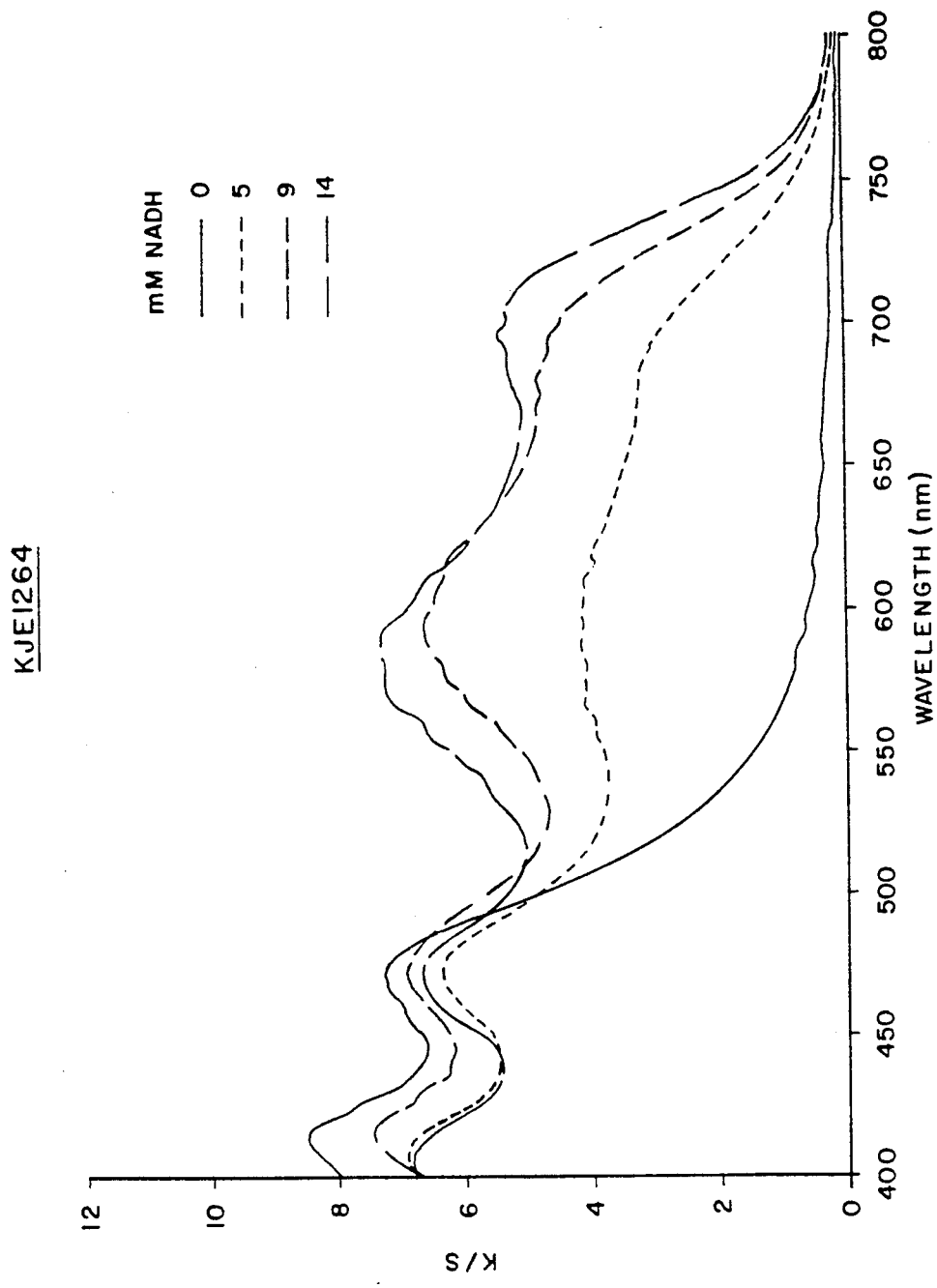
FIG. 5 shows the corresponding spectrum for the formazan from the present compound 2-(4,5-bis(4-methoxyphenyl)-thiazol-2-yl)-3-(4-carboxyphenyl)-5-(2-thienyl) tetrazolium salt (KJE1264).

With reference to the drawing, FIGS. 1–4 show the reflectance spectra of the formazans produced upon reduction of the prior art tetrazolium salts INT, MTT, and NBT at various concentrations of glucose. For purposes of comparison, FIG. 5 shows the corresponding spectrum for the present compound (KJE1264) (see item A-1-a in the Table below) when tested with various levels of NADH. The presence of a plateau in the spectra of the formazans from the present compounds, and its absence from that of the formazans from the prior art compounds, is readily apparent. The four above-mentioned prior art compounds exhibit percent changes in K/S over the wavelength range 650–700 nm as follows:

| | |
|---|---|
| INT | 71% |
| MTT | 178% |
| NBT | 73% |
| USSR | 28% |

The lower the percent K/S value for the formazan, the more tolerant is the tetrazolium salt to variations in the central wavelength of the optical system used to measure reflectance, and hence to measure analyte concentration. The following non-standard abbreviations are used in the text below:

"UV"—The wavelength in nanometers of maximum reflectance peak in the UV reflectance spectrum of the formazan. The extinction coefficient and solvent used during measurement are given in parentheses.

"nm"—The position of the flattest portion of the reflectance spectrum of the formazan over a 50 nm wavelength span (expressed as the beginning and ending wavelengths in nanometers).

"K/S"—The percent change in K/S units over the above mentioned flattest 50 nm portion of the reflectance spectrum. The concentration of analyte used to generate the reflectance spectrum is given in parentheses. Mmol refers to the concentration in mmol/liter.

TABLE

A. 4,5-bis(4-methoxyphenyl)thiazol-2-yl

1 $R^4$=4-carboxyphenyl
 a) $R^3$=2-thienyl (KJE1264); UV: 623 (11.6×10³, water); nm: 660–710 nm; K/S: 9% (14 mmol)

B. 4,5-diphenylthiazol-2-yl

1. $R^4$=4-carboxyphenyl
 a) $R^3$=3,4-methylenedioxyphenyl; UV: 495 (12.6×10³, water); nm: 630–680 nm; K/S: 16% (15 mmol)
 b) $R^3$=4-methoxyphenyl; UV: 613 (8.66×10³, water); nm: 630–680 nm; K/S: 17% (8 mmol)
 c) $R^3$=2-thienyl; UV: 602 (8.22×10³, water); nm: 635–685 nm; K/S: 18% (9 mmol)
 d) $R^3$=3-thienyl; UV: 599 (11.8×10³, water)
 e) $R^3$=4-fluorophenyl; UV: 592 (13.6×10³, water); nm: 625–675 nm; K/S: 11% (33 mmol)
 f) $R^3$=4-hydroxyphenyl; UV: 620 (11.2×10³, water)
 *g) $R^3$=phenyl; UV: 420, 590 (water); nm: 610–660 nm; K/S: 38% (14 mmol)

2. $R^4$=phenyl
 a) $R^3$=2-thienyl; UV: 571 (9×10³, water); nm: 640–690 nm; K/S: 4% (14 mmol)

3. $R^4$=3-pyridyl
 a) $R^3$=4-methoxyphenyl; UV: 589 (11.8×10³, water); nm: 620–670 nm; K/S: 15% (15 mmol)

4. $R^4$=8-quinolyl
 a) $R^3$=phenyl; UV: 607 (14.4×10³, water); nm: 620–680 nm; K/S: 21% (15 mmol)

5. $R^4$=4-nitronaphthyl
 a) $R^3$=3-thienyl; UV: 696 (10.4×10³, water); nm: 620–670 nm; K/S: 12% (14 mmol)

6 $R^4$=4-sulfophenyl
 a) $R^3$=2-thienyl; UV: 610 (6.0×10³, water)

7. $R^4$=3,5-dicarboxyphenyl
 a) $R^3$=3,4-methylenedioxyphenyl; UV: 597 (5.2×10³, water); nm: 620–670 nm; K/S: 7% (14 mmol)

8. $R^4$=4-nitrophenyl
 a) $R^3$=3,4-methylenedioxyphenyl; nm: 640–690 nm; K/S: 8.3% (14 mmol)

9. $R^4$=8-quinolyl
 a) $R^3$=2-thienyl; nm: 640–690 nm; K/S: 5.7% (14 mmol)

*10. $R^4$=2-carboxyphenyl
 a) $R^3$=phenyl; UV: 420; nm: 600–650 nm; K/S: 42% (14 mmol)
 b) $R^3$=pyridyl-3; UV: nm: 610–660 nm; K/S: 39%

*11. $R^4$=3-carboxyphenyl
 a) $R^3$=phenyl; UV: 420, 590; nm: 610–660 nm; K/S: 18% (14 mmol)

C. 4-phenylthiazol-2-yl

1. $R^4$=3,4,5-trimethoxyphenyl
 a) $R^3$=3,4-methylenedioxyphenyl; nm: 645–695 nm; K/S: 28% (8.3 mmol)

2. $R^4$=4-carboxyphenyl
 a) $R^3$=3,4-methylenedioxyphenyl; nm: 620–670 nm; K/S: 11% (8.3 mmol)

D. 4-(p-fluorophenyl)thiazol-2-yl

1. $R^4$=3,4,5-trimethoxyphenyl
 a) $R^3$=3,4-methylenedioxyphenyl; nm: 645–695 nm; K/S: 19% (8.3 mmol)

2. $R^4$=4-carboxyphenyl
 a) $R^3$=3,4-methylenedioxyphenyl; nm: 625–675 nm; K/S: 12% (8.3 mmol)

E. 4-phenyl-5-methylthiazol-2-yl

1. $R^4$=3,4,5-trimethoxyphenyl
 a) $R^3$=3,4-methylenedioxyphenyl; nm: 625–675 nm; K/S: 22% (8.3 mmol)

2. $R^4$=4-carboxyphenyl
 a) $R^3$=2-thienyl; nm: 600–650 nm; K/S: 10% (10.3 mmol)
 b) $R^3$=4-methylphenyl; nm: 580–630 nm; K/S: 5% (10.3 mmol)

F. 4-naphthyl-5-phenylthiazol-2-yl

1. $R^4$=4-carboxyphenyl
 a) $R^3$=3,4-methylenedioxyphenyl; nm: 620–670 nm; K/S: 10% (8.3 mmol)
 b) $R^3$=2-thienyl; nm: 600–650 nm; K/S: 4% (10.3 mmol)

G. 4-styryl-5-phenylthiazol-2-yl

1. $R^4$=3,4,5-trimethoxyphenyl
 a) $R^3$=3,4-methylenedioxyphenyl nm: 670–720 nm; K/S: 21% (10.3 mmol)

*Prior art compounds for comparison.

The present invention has been particularly described and exemplified above. Clearly, other variations and modifications of the invention can be made without departing from the spirit and scope hereof.

What is claimed is:

1. Phenyl substituted 2-thiazolyl tetrazolium salt indicators characterized by the formula:

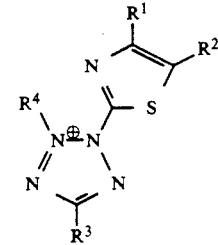

wherein $R^1$ and $R^2$ are such that the 2-thiazolyl group is 4,5-bis(4-methoxyphenyl)thiozol-2-yl; 4,5-diphenylthiazol-2-yl; 4-phenylthiazol-2-yl; 4-phenyl-5-methylthiazol-2-yl or 4-naphthyl-5-phenylthiazol-2-yl; wherein $R^4$ is 4-carboxyphenyl; phenyl; 3-pyridyl; 4-nitrophenyl; 3,5-dicarboxyphenyl; 4-nitrophenyl; 8-quinolyl; or 3,4,5-trimethoxyphenyl; wherein $R^3$ is 3-4-methylenedioxyphenyl; 4-methoxyphenyl; 2-thienyl, 4-fluorophenyl; or 3-thienyl and $X^\ominus$ is a counteranion and wherein the compounds are further characterized in that the reflectance spectra exhibited by each of said compounds when reduced to its colored formazan state varies by less than about 17% over a wavelength range of 50 nm when the midpoint of the 50 nm range is 640 nm or greater.

2. A tetrazolium indicator compound as characterized by claim 1 wherein $R^1$ and $R^2$ are such that the 2-thiazolyl group is 4,5-bis(4-methoxyphenyl)thiazol-2-yl; $R^4$ is 4-carboxyphenyl and $R^3$ is 2-thienyl.

3. Tetrazolium indicator compounds as characterized by claim 1 wherein $R^1$ and $R^2$ are such that the 2-thiazolyl group is 4,5-diphenylthiazol-2-yl; $R^4$ is 4-carboxyphenyl; phenyl, 3-pyridyl; 4-nitronaphthyl; 3,5-dicarboxyphenyl; 4-nitrophenyl or 8-quinolyl and $R^3$ is 3,4- methylenedioxyphenyl; 4-methoxyphenyl; 2-thienyl or 3-thienyl.

4. Tetrazolium indicator compounds as characterized by claim 3 wherein $R^4$ is carboxyphenyl and $R^3$ is 3,4-methylenedioxyphenyl; 4-methoxyphenyl or 2-thienyl.

5. A tetrazolium indicator compound as characterized by claim 3 wherein $R^4$ is phenyl and $R^3$ is 2-thienyl.

6. A tetrazolium indicator compound as characterized by claim 3 wherein $R^4$ is 3-pyridyl and $R^3$ is 4-methyoxyphenyl.

7. A tetrazolium indicator compound as characterized by claim 3 wherein $R^4$ is 4-nitrophenyl and $R^3$ is 3,4-methylenedioxyphenyl.

8. A tetrazolium indicator compound as characterized by claim 3 wherein $R^4$ is 4-nitronaphthyl and $R^3$ is 3-thienyl.

9. A tetrazolium indicator compound as characterized by claim 3 wherein $R^4$ is 3,5-dicarboxyphenyl and $R^3$ is 3,4-methylenedioxyphenyl.

10. A tetrazolium indicator compound as characterized by claim 2 wherein $R^4$ is 8-quinolyl and $R^3$ is 2-thienyl.

11. A tetrazolium indicator compound as characterized by claim 1 wherein $R^1$ and $R^2$ are such that the 2-thiazolyl group is 4-phenylthiazol-2-yl; $R^4$ is 4-carboxyphenyl and $R^3$ is 3,4-methylenedioxyphenyl.

12. A tetrazolium indicator compound as characterized by claim 1 wherein $R^1$ and $R^2$ are such that the 2-thiazolyl group is 4-(p-fluorophenyl)thiazol-2-yl; $R^4$ is 4-carboxyphenyl and $R^3$ is 3,4-methylenedioxyphenyl.

13. Tetrazolium indicator compounds as characterized by claim 1 wherein $R^1$ and $R^2$ are such that the 2-thiazolyl group is 4-phenyl-5-methylthiazol-2-yl; $R^4$ is 4-carboxyphenyl and $R^3$ is 2-thienyl or 4-methylphenyl.

14. Tetrazolium indicator compounds as characterized by claim 1 wherein $R^1$ and $R^2$ are such that the 2-thiazolyl group is 4-naphthyl-5-phenylthiazol-2-yl; $R^4$ is 4-carboxyphenyl and $R^3$ is 3,4-methylenedioxyphenyl or 2-thienyl.

15. In the method of detecting a reducing substance by contacting such substance with a tetrazolium salt which is reducible by the reducing substance to a formazan dye which can be detected colorimetrically, the improvement which comprises using one or more of the tetrazolium salts of claims 1–13 in such procedure.

16. The method of claim 15 wherein the reducing substance is NADH.

17. The method of claim 15 wherein the reducing substance is hydrogen sulfide, diborane, arsenic hydride or phosphorus hydride.

* * * * *